United States Patent
Kawamura et al.

(10) Patent No.: US 9,499,460 B2
(45) Date of Patent: Nov. 22, 2016

(54) ALCOHOL PRODUCTION METHOD

(71) Applicant: Toray Industries, Inc., Tokyo (JP)

(72) Inventors: Kenji Kawamura, Kamakura (JP); Masateru Ito, Kamakura (JP); Satoshi Sakami, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/653,382

(22) PCT Filed: Dec. 18, 2013

(86) PCT No.: PCT/JP2013/083829
§ 371 (c)(1),
(2) Date: Jun. 18, 2015

(87) PCT Pub. No.: WO2014/098105
PCT Pub. Date: Jun. 26, 2014

(65) Prior Publication Data
US 2016/0185694 A1 Jun. 30, 2016

(30) Foreign Application Priority Data

Dec. 19, 2012 (JP) .................................. 2012-276576

(51) Int. Cl.
*C07C 29/76* (2006.01)
*C07C 29/80* (2006.01)

(52) U.S. Cl.
CPC .............. *C07C 29/76* (2013.01); *C07C 29/80* (2013.01)

(58) Field of Classification Search
CPC ....... C07C 29/76; C07C 31/10; C07C 31/12; C07C 31/205; C07C 31/207; C07C 29/80; B01D 61/04; B01D 2311/2623
See application file for complete search history.

(56) References Cited

U.S. PATENT DOCUMENTS

| | | | |
|---|---|---|---|
| 6,428,992 B1 | 8/2002 | Roturier et al. | |
| 6,603,048 B1 * | 8/2003 | Corbin | B01D 15/00 568/868 |
| 7,713,418 B2 | 5/2010 | Frank et al. | |
| 2005/0069997 A1 | 3/2005 | Adkesson et al. | |
| 2007/0193960 A1 | 8/2007 | Frank et al. | |
| 2011/0152581 A1 | 6/2011 | Adkesson et al. | |
| 2011/0152583 A1 | 6/2011 | Adkesson et al. | |

FOREIGN PATENT DOCUMENTS

| | | |
|---|---|---|
| JP | 2007-525508 A | 9/2007 |
| JP | 2010-143888 A | 7/2010 |
| JP | 2010-150248 A | 7/2010 |
| JP | 2010-253357 A | 11/2010 |
| JP | 2011-126911 A | 6/2011 |
| WO | 2004/101479 A2 | 11/2004 |
| WO | 2005/087692 A2 | 9/2005 |

OTHER PUBLICATIONS

Notification of the First Office Action dated Mar. 14, 2016, of corresponding Chinese Application No. 2013800665136, along with an English translation.
Supplementary European Search Report dated Jun. 23, 2016, of corresponding European Application No. 13864516.3.

* cited by examiner

Primary Examiner — Jafar Parsa
(74) Attorney, Agent, or Firm — DLA Piper LLP (US)

(57) ABSTRACT

An alcohol production method whereby high quality alcohol can be easily and effectively produced includes a step in which an alcohol solution, which contains sugar and/or sugar alcohol as an impurity and an alcohol other than sugar alcohol as a main component, has the sugar and/or sugar alcohol adsorptively removed therefrom by contacting the alcohol solution with one type or a mixture of two or more types of adsorbents selected from zeolite, an ion-exchange resin, silica alumina, and alumina.

16 Claims, No Drawings

ALCOHOL PRODUCTION METHOD

TECHNICAL FIELD

This disclosure relates to a method of producing an alcohol by separating an alcohol that is a main component in an alcohol solution from sugar and/or sugar alcohol that are impurities.

BACKGROUND

Alcohols are industrially a very important compound as raw materials for chemicals and pharmaceuticals, solvents and fuels. As a method of producing an alcohol, for butanol, for example, a method by synthesis from acetaldehyde by the Wacker process, and a method by industrial production from propylene, carbon monoxide and water by the Reppe process are utilized. As other examples, for 1,4-butanediol, a production method by reacting acetylene with formaldehyde, followed by hydrogenation, and a production method by reacting butadiene with acetic acid in the presence of a palladium catalyst, followed by reduction and hydrolysis are well-known. Besides those chemical synthesis methods, the conversion into a production method derived from biomass such as a fermentation process, is expected in recent years due to the decrease and price rise of oil resources, and a technique of producing a non-petroleum-derived alcohol in high purity and at low cost is required.

As a purification method of an alcohol, solvent extraction and distillation are generally known. In the solvent extraction, when the object is a lower alcohol, it is difficult to distribute it into an organic phase due to high water solubility. Therefore, specific extraction solvent and multistage extraction are required, and this leads to the problem of the increase of costs (Japanese Translated PCT Patent Application Laid-open No. 2007-525508). Furthermore, it is known that an alcohol produced by a fermentation process contains sugars as a nutrient source for microorganisms, and sugar alcohol, organic acids, inorganic salts, proteins and the like as metabolites, and that coloring impurities are generated as a by-product, by heating. For this reason, when an alcohol is purified with distillation, there are problems in the decrease of distillation yield by those impurities and the deterioration of quality due to the contamination of the coloring impurities into the purified alcohol. Furthermore, JP 2010-150248 A and JP 2010-143888 A disclose a method of separating diol, triol or butanol from sugars by a nanofiltration membrane, but there still remains a problem regarding their recovery. For this reason, a technique of efficiently recovering high quality alcohol while reducing impurities such as sugar and sugar alcohol contained in an alcohol solution is required.

It could therefore be helpful to provide a method of producing high quality alcohol by reducing sugar or sugar alcohol conveniently and efficiently in separating an alcohol from an alcohol solution which contains sugar and/or sugar alcohol as impurities.

SUMMARY

We found that sugar and/or sugar alcohol contained in an alcohol solution can be reduced by adsorption and removal with an adsorbent such as zeolite, an ion-exchange resin, silica-alumina or alumina.

We thus provide the following (1) to (10).

(1) A method of producing an alcohol, comprising a step of contacting an alcohol solution comprising sugar and/or sugar alcohol as impurities and comprising an alcohol other than sugar alcohol as a main component, with one kind or a mixture of two or more kinds selected from zeolite, an ion-exchange resin, silica-alumina and alumina, thereby adsorbing and removing the sugar and/or sugar alcohol.

(2) The method of producing an alcohol according to (1), wherein the alcohol other than sugar alcohol is a monohydric or dihydric alcohol.

(3) The method of producing an alcohol according to (1) or (2), wherein the alcohol other than sugar alcohol is an alcohol having 2 to 6 carbon atoms.

(4) The method of producing an alcohol according to any one of (1) to (3), wherein the alcohol other than sugar alcohol is one kind or a mixture of two or more kinds selected from ethanol, ethylene glycol, isopropanol, 1,3-propanediol, n-butanol, 2-butanol, isobutanol, 1,4-butanediol, 2,3-butanediol and 1,6-hexanediol.

(5) The method of producing an alcohol according to any one of (1) to (4), wherein a concentration of the alcohol other than sugar alcohol in the alcohol solution is 50 weight % or more.

(6) The method of producing an alcohol according to any one of (1) to (5), wherein the alcohol solution contains glucose, fructose or xylose as impurities.

(7) The method of producing an alcohol according to any one of (1) to (6), wherein the alcohol solution contains glycerol, xylitol or erythritol as impurities.

(8) The method of producing an alcohol according to any one of (1) to (7), wherein an inlet pore diameter of the zeolite is larger than 5 angstroms.

(9) The method of producing an alcohol according to any one of (1) to (7), wherein the ion-exchange resin is a strongly basic ion-exchange resin.

(10) The method of producing an alcohol according to any one of (1) to (9), further comprising a step of distilling the alcohol solution from which the sugar and/or sugar alcohol have been adsorbed and removed.

Sugar and/or sugar alcohol contained in an alcohol solution can thus be reduced efficiently and at low cost by simple operations, and high quality alcohol in which coloration due to heating during distillation has been reduced can be obtained.

DETAILED DESCRIPTION

A method of producing an alcohol comprises a step of removing, sugar impurities from an alcohol solution comprising sugar and/or sugar alcohol (hereinafter simply referred to as "sugar impurities") as impurities and comprising an alcohol other than sugar alcohol as a main component, by an adsorbent such as zeolite, an ion-exchange resin, silica-alumina or alumina. Our methods are described in more detail below.

An "alcohol other than sugar alcohol" means a compound having one or more hydroxyl groups (OH group) in the molecule and not being sugar alcohol described hereinafter, and is not particularly limited. The alcohol may be one kind and may be a mixture of plural kinds.

A preferred alcohol is preferably a monohydric or dihydric alcohol, and preferably has 2 to 6 carbon atoms. Specific examples of the preferred alcohol include saturated aliphatic compounds such as ethanol, ethylene glycol, 1-propanol, isopropanol, 1,2-propanediol, 1,3-propanediol, n-butanol, 2-butanol, isobutanol, 1,3-butanediol, 1,4-butanediol, 2,3-butanediol, 1,5-pentanediol and 1,6-hexanediol; unsaturated aliphatic compounds such as propenediol and butenediol; aromatic compounds such as catechol and resorcinol; saturated alicyclic compounds such as cyclopropanol, cyclopropanediol, cyclobutanol, cyclobutanediol, cyclopentanol, cyclopentanediol, cyclohexanol and cyclohexanediol; and unsaturated alicyclic compounds such as cyclobutenol, cyclobutenediol, cyclopentenol, cyclopentenediol, cyclohexenol and cyclohexenediol. Saturated aliphatic compounds are more preferred, and ethanol, ethylene glycol, isopropanol, 1,3-propanediol, n-butanol, 2-butanol, isobutanol, 1,3-butanediol, 1,4-butanediol, 2,3-butanediol and 1,6-hexanediol are still more preferred.

The sugar contained as sugar impurities is a compound having an aldehyde group or a ketone group in the molecule, and examples thereof specifically include glucose, mannose, galactose, fructose and xylose. Among those, glucose, fructose and xylose are preferred.

The sugar alcohol contained as sugar impurities means a compound in which carbonyl groups of the above-mentioned sugars have been reduced, and examples thereof specifically include glycerol, erythritol, xylitol, sorbitol and mannitol. Among those, glycerol, xylitol and erythritol are preferred.

An "alcohol solution comprising sugar and/or sugar alcohol as impurities and comprising an alcohol other than sugar alcohol as a main component" is not particularly limited so long as it is a solution containing an alcohol as a main component and containing sugar impurities as impurities, and may be an alcohol aqueous solution. The alcohol and sugar or sugar alcohol contained in the alcohol solution can be quantified by high performance liquid chromatography (HPLC).

A method of producing the "alcohol solution comprising sugar and/or sugar alcohol as impurities and comprising an alcohol other than sugar alcohol as a main component" is not particularly limited so long as it is the conventional method of one skilled in the art, and the alcohol solution may be one obtained by chemical synthesis, or may be an alcohol fermentation culture liquid itself obtained by microbial fermentation and may be one through a plurality of separation and purification steps from the alcohol fermentation culture liquid. However, since the alcohol solution derived from the alcohol fermentation culture liquid contains a sugar component in a culture component due to fermentation culture, sugar impurities may be contained in a larger amount as compared to one derived from chemical synthesis. Therefore, it is preferred that the alcohol solution is produced by microbial fermentation.

The step of removing sugar impurities contained in the alcohol solution by an adsorbent such as zeolite, an ion-exchange resin, silica-alumina or alumina is characterized in that sugar impurities contained in the alcohol solution are adsorbed in an adsorbent. The above-mentioned adsorbent is generally utilized for the purpose of adsorption of a low polarity compound in a high polarity solvent, adsorption of a high polarity compound in a low polarity solvent and adsorption of an ionic component utilizing ion-exchange function represented by an ion-exchange resin, but the characteristic resides in the finding that sugar and sugar alcohol that are high polarity compounds contained in an alcohol solution having high polarity can be adsorbed and removed. Of the above adsorbents, zeolite and an ion-exchange resin have excellent adsorption capability and are therefore preferred.

The zeolite is not particularly limited, and specific examples thereof that can be used include the conventional ones such as A-type, X-type, Y-type, ZSM-type, beta-type, ferrierite, mordenite, faujasite and montmorillonite. Pore diameter of the zeolite is not particularly limited. However, ones with the pore diameter of larger than 5 angstroms are preferred because adsorption efficiency on the surface inside pores is increased, and adsorption amount is increased. Regarding cation species of the zeolite, any of H-type, Na-type, K-type, Ca-type, $NH_4$-type and the like can be used. In Na-type and K-type, adsorption efficiency is increased, and those can be preferably used. As the zeolite, any of powdery one and granulated one can be used. The granulated zeolite can be preferably used from that operability and solid-liquid separability are excellent.

The ion-exchange resin is not particularly limited, and any of strongly acidic (cation-exchange resin), strongly basic (anion-exchange resin), weakly acidic (cation-exchange resin), weakly basic (anion-exchange resin), and salt forms of those can be used. Strongly basic ion-exchange resin is preferred due to excellent sugar or sugar alcohol adsorption capability, and OH-type strongly basic ion-exchange resin is particularly preferred. As those ion-exchange resins, any of a gel type and a porous type resin can be used.

A method of contacting an alcohol solution with an adsorbent can employ any system of a batchwise system (stirring tank system) and a column system (fixed bed flow system). The column system is preferred due to good operability. Furthermore, temperature during the contact of the alcohol solution with the adsorbent is not particularly limited, and those can be suitably used at normal temperature.

The adsorbent used in the removal of sugar impurities can be regenerated by washing with water. In general, when an ion component has been adsorbed on an ion-exchange resin, washing with chemicals such as an acid or an alkali is necessary for regeneration. However, since the adsorbent having sugar impurities as non-ion components adsorbed thereon can be regenerated by washing with water having high polarity, the cost of chemicals necessary for the regeneration of the adsorbent can be reduced. Water used to generate the adsorbent is not particularly limited. However, when water containing many ion components has been used, counter ions on the surface of the adsorbent are exchanged with the ion components, and there is a possibility that adsorption effect of sugar impurities is deteriorated. For this reason, washing using ion-exchange water is preferably applied.

Alcohol concentration of the alcohol solution subjected to adsorption treatment by an adsorbent is not particularly limited. However, when moisture concentration is higher than 50 weight %, adsorption of sugar or sugar alcohol onto the adsorbent is suppressed by the influence of water having highly polarity. Therefore, it is preferred that the alcohol concentration is concentrated to 50 weight % or more by concentration operation, and the alcohol solution is then treated with the adsorbent.

As a method of concentrating the alcohol solution, water can be evaporated by heating and reducing pressure with a concentrating apparatus represented by an evaporator and alcohol concentration can be increased by a reverse osmosis membrane. Because energy required for concentration can be reduced, the concentrating method by a reverse osmosis membrane is preferred, and when an alcohol having a boiling point lower than that of water is concentrated, the concentration by a reverse osmosis membrane is particularly preferred. The reverse osmosis membrane used herein is a filtration membrane that can filter out ions and low molecular weight molecules by utilizing pressure difference equal to or more than osmotic pressure of a non-treating liquid as driving power. In the concentration of the alcohol solution by a reverse osmosis membrane, an alcohol solution having increased alcohol concentration at a non-permeation side can be obtained by permeating moisture in the alcohol solution into a permeation side of the reverse osmosis membrane.

As membrane material of the reverse osmosis membrane for the concentration of an alcohol solution, polymer materials such as generally commercially available cellulose acetate polymer, polyamide, polyester, polyimide, and vinyl polymer can be used. However, the membrane is not limited to a membrane constituted of one kind of the materials, and may be a membrane containing a plurality of membrane materials. Furthermore, the membrane structure may be any of an asymmetric membrane having a dense layer on at least one surface of the membrane and having fine pores which have pore diameters gradually increasing from the dense layer toward the inside of the membrane or the other surface, and a composite membrane having a very thin functional layer formed of other material on the dense layer of the asymmetric membrane. As membrane form of the reverse osmosis membrane, an appropriate form such as a flat membrane type, a spiral type or a hollow fiber type can be used.

Specific examples of the reverse osmosis membrane include polyamide reverse osmosis membranes UTC-70, SU-710, SU-720, SU-720F, SU-710L, SU-720L, SU-720LF, SU-720R, SU-710P, SU-720P, SU-810, SU-820, SU-820L, SU-820FA, SU-610, SU-620, TM800, TM800C, TM800A, TM800H, TM800E and TM800L, manufactured by Toray Industries, Inc.; cellulose acetate reverse osmosis membranes SC-L100R, SC-L200R, SC-1100, SC-1200, SC-2100, SC-2200, SC-3100, SC-3200, SC-8100 and SC-8200, manufactured by Toray Industries, Inc.; NTR-759HR, NTR-729HF, NTR-70SWC, ES10-D, ES20-D, ES20-U, ES15-D, ES15-U and LF10-D, manufactured by Nitto Denko Corporation; RO98pHt, R099, HR98PP, CE4040C-30D, NF99 and NF99HF, manufactured by Alfa Laval; GE Sepa, OSMO BEV NF Series, HL Series, Duraslick Series, MUNI NF Series, CK Series, DK Series, Seasoft Series and Duratherm HWS Series, manufactured by GE; Se1RO Series, manufactured by KOCH; and BW30-4040, TW30-4040, XLE-4040, LP-4040, LE-4040, SW30-4040, SW30HRLE-4040, NF45, NF90, NF200 and NF400, manufactured by Filmtec.

By further subjecting the alcohol solution obtained by the adsorption treatment step by an adsorbent to a distillation step and recovering an alcohol from a steam side, sugar or sugar alcohol can be further reduced, and low coloration and high purity alcohol can be purified. Alcohol concentration of the alcohol solution to be subjected to a distillation step is not particularly limited. The alcohol solution obtained by an adsorbent treatment may be directly distilled, or it may be subjected to a concentrating step by an evaporator or the above-described reverse osmosis membrane, followed by distillation. Pressure and temperature during distillation are not particularly limited, and depending on the kind of an alcohol, the distillation can be performed under a pressure of from 1 Pa to atmospheric pressure (normal pressure, about 101 kPa) at a temperature of from 20° C. to 250° C.

EXAMPLES

Our methods are described in more detail below by reference to examples, but this disclosure is not construed as being limited to the following examples.

Examples 1 to 27

Adsorption Removal Test of Sugar in Alcohol Solution by Adsorbent

Pure water and sugar (glucose, fructose or xylose, all manufactured by Wako Pure Chemical Industries, Ltd.) were added to n-butanol (Examples 1 to 9), 1,4-butanediol (Examples 10 to 18), isopropanol (Examples 19 to 21), ethanol (Examples 22 to 24) and 1,3-propanediol (Examples 25 to 27) (all manufactured by Wako Pure Chemical Industries, Ltd.) to prepare 50 g of alcohol solutions having various alcohol and sugar concentrations. Subsequently, to 50 g of the alcohol solution was added as an adsorbent, 5 g of any of NaX type zeolite (F-9, manufactured by Tosoh Corporation), NaY type zeolite (HSZ-300, manufactured by Tosoh Corporation) and "DIAION" SA10AOH (OH-type strongly basic ion-exchange resin, manufactured by Mitsubishi Chemical Corporation), followed by stirring at room temperature for 1 hour. Sugar concentration in the alcohol solution before and after the adsorbent treatment was measured with high performance liquid chromatography, and sugar adsorption removal rate was calculated by the method of Formula (1).

Sugar adsorption removal rate (%)=100×(sugar concentration (g/L) before adsorbent treatment− sugar concentration (g/L) after adsorbent treatment)/sugar concentration (g/L) before adsorbent treatment       (1)

The sugar concentration in the alcohol solution was measured under the following conditions by high performance liquid chromatography (manufactured by Shimadzu Corporation). The results are shown in Table 1.

Column: Shodex Asahipak NH2P-50 (manufactured by Showa Denko K.K.)

Mobile phase: Acetonitrile:water=3:1 (vol/vol)

Flow rate: 0.6 mL/min

Detection method: Differential refractive index detector (RI)

Column temperature: 30° C.

Comparative Examples 1 to 6

Adsorption Removal Test of Sugar in Alcohol Solution by Diatomaceous Earth

Pure water and 0.5 wt % sugar (glucose, fructose or xylose, all manufactured by Wako Pure Chemical Industries, Ltd.) based on an alcohol were added to n-butanol (Comparative Examples 1 to 3) and 1,4-butanediol (Comparative Examples 4 to 6) (both manufactured by Wako Pure Chemical Industries, Ltd.) to prepare 50 g of 85 wt % alcohol solutions. Subsequently, to 50 g of the alcohol solutions was added 5 g of diatomaceous earth (Celite 545, manufactured by Kanto Chemical Co., Inc.), followed by stirring at room temperature for 1 hour. Sugar concentration in the alcohol solution before and after diatomaceous earth treatment was measured under the same conditions as in Examples 1 to 27 with high performance liquid chromatography (manufactured by Shimadzu Corporation), and sugar adsorption removal rate was calculated according to Formula (1). The results are shown in Table 1.

TABLE 1

|  | Alcohol | Sugar | Sugar/alcohol (wt %) | Moisture concentration (wt %) | Adsorbent | Removal rate (%) |
|---|---|---|---|---|---|---|
| Ex. 1 | n-Butanol | Glucose | 0.5 | 15 | NaX | 65 |
| Ex. 2 |  |  | 0.5 | 15 | NaY | 43 |
| Ex. 3 |  |  | 0.5 | 15 | SA10AOH | 100 |
| Ex. 4 |  | Fructose | 0.5 | 15 | NaX | 67 |
| Ex. 5 |  |  | 0.5 | 15 | NaY | 49 |
| Ex. 6 |  |  | 0.5 | 15 | SA10AOH | 100 |
| Ex. 7 |  | Xylose | 0.5 | 15 | NaX | 45 |
| Ex. 8 |  |  | 0.5 | 15 | NaY | 24 |
| Ex. 9 |  |  | 0.5 | 15 | SA10AOH | 99 |
| Ex. 10 | 1,4-Butanediol | Glucose | 4 | 25 | NaX | 43 |
| Ex. 11 |  |  | 4 | 25 | NaY | 26 |
| Ex. 12 |  |  | 0.5 | 15 | SA10AOH | 94 |
| Ex. 13 |  | Fructose | 4 | 25 | NaX | 39 |
| Ex. 14 |  |  | 4 | 25 | NaY | 30 |
| Ex. 15 |  |  | 0.5 | 15 | SA10AOH | 93 |
| Ex. 16 |  | Xylose | 4 | 25 | NaX | 29 |
| Ex. 17 |  |  | 4 | 25 | NaY | 14 |
| Ex. 18 |  |  | 0.5 | 15 | SA10AOH | 49 |
| Ex. 19 | Isopropanol | Glucose | 0.5 | 15 | SA10AOH | 100 |
| Ex. 20 |  | Fructose | 0.5 | 15 | SA10AOH | 100 |
| Ex. 21 |  | Xylose | 0.5 | 15 | SA10AOH | 97 |
| Ex. 22 | Ethanol | Glucose | 0.5 | 15 | SA10AOH | 100 |
| Ex. 23 |  | Fructose | 0.5 | 15 | SA10AOH | 98 |
| Ex. 24 |  | Xylose | 0.5 | 15 | SA10AOH | 100 |
| Ex. 25 | 1,3-Propanediol | Glucose | 0.5 | 15 | SA10AOH | 88 |
| Ex. 26 |  | Fructose | 0.5 | 15 | SA10AOH | 85 |
| Ex. 27 |  | Xylose | 0.5 | 15 | SA10AOH | 86 |
| Comp. Ex. 1 | n-Butanol | Glucose | 0.5 | 15 | Diatomaceous earth | 4 |
| Comp. Ex. 2 |  | Fructose | 0.5 | 15 | Diatomaceous earth | 5 |
| Comp. Ex. 3 |  | Xylose | 0.5 | 15 | Diatomaceous earth | 1 |
| Comp. Ex. 4 | 1,4-Butanediol | Glucose | 0.5 | 15 | Diatomaceous earth | 1 |
| Comp. Ex. 5 |  | Fructose | 0.5 | 15 | Diatomaceous earth | 2 |
| Comp. Ex. 6 |  | Xylose | 0.5 | 15 | Diatomaceous earth | 4 |

As shown in Table 1, we found that the alcohol solution having efficiently reduced sugar can be obtained by treating an alcohol solution containing sugar with zeolite and an ion-exchange resin.

Examples 28 to 72

Adsorption Removal Test of Sugar Alcohol in Alcohol Solution by Adsorbent

Pure water and sugar alcohol (glycerol or xylitol, both manufactured by Wako Pure Chemical Industries, Ltd.) were added to n-butanol (Examples 28 to 44), 1,4-butanediol (Examples 45 to 51), isopropanol (Examples 52 to 58), ethanol (Examples 59 to 65) and 1,3-propanediol (Examples 66 to 72) (all manufactured by Wako Pure Chemical Industries, Ltd.) to prepare 50 g of alcohol solutions having various alcohol and sugar alcohol concentrations. Subsequently, to 50 g of the alcohol solution was added as a adsorbent, 5 g of any of NaX type zeolite (F-9, manufactured by Tosoh Corporation), $NH_4$ type ZSM-5 zeolite (HSZ-800, Type 840NHA, manufactured by Tosoh Corporation), K-type ferrierite (HSZ-600, Type 720KOA, manufactured by Tosoh Corporation), NaY type zeolite (HSZ-300, manufactured by Tosoh Corporation), amorphous silica-alumina (N633HN, manufactured by JGC Catalysts and Chemicals Ltd.), alumina (N613N, manufactured by JGC Catalysts and Chemicals Ltd.), "DIAION" SA10A (CL-type strongly basic ion-exchange resin, manufactured by Mitsubishi Chemical Corporation), "DIAION" SA10AOH (OH-type strongly basic ion-exchange resin, manufactured by Mitsubishi Chemical Corporation), "DIAION" WA20 (weakly basic ion-exchange resin, manufactured by Mitsubishi Chemical Corporation), "DIAION" SK1B (Na-type strongly acidic ion-exchange resin, manufactured by Mitsubishi Chemical Corporation) and "DIAION" SK1BH (H-type strongly acidic ion-exchange resin, manufactured by Mitsubishi Chemical Corporation), followed by stirring at room temperature for 1 hour. Sugar alcohol concentration in the alcohol solution before and after the adsorbent treatment was measured with high performance liquid chromatography, and sugar alcohol adsorption removal rate was calculated by the method of Formula (2).

Sugar alcohol adsorption removal rate (%)=100×
(sugar alcohol concentration (g/L) before adsorbent treatment−sugar alcohol concentration (g/L) after adsorbent treatment)/sugar concentration (g/L) before adsorbent treatment    (2)

The sugar alcohol concentration in the alcohol solution was measured under the same conditions as in Examples 1 to 27 by high performance liquid chromatography (manufactured by Shimadzu Corporation). The results are shown in Table 2.

Comparative Examples 7 to 12

Adsorption Removal Test of Sugar Alcohol in Alcohol Solution by Diatomaceous Earth and Activated Carbon Pure water and sugar alcohol (glycerol or xylitol, both manufactured by Wako Pure Chemical Industries, Ltd.) were added to n-butanol (Comparative Examples 7 to 9) and 1,4-butanediol (Comparative Examples 10 to 12) (both manufactured by Wako Pure Chemical Industries, Ltd.) to prepare 50 g of alcohol solutions having various alcohol and sugar alcohol concentrations. Subsequently, to 50 g of the alcohol solution was added 5 g of diatomaceous earth ("Celite 545", manufactured by Kanto Chemical Co., Inc.) or 0.1 g of activated carbon ("SHIRASAGI A", manufactured by Japan Enviro Chemicals, Ltd.), followed by stirring at room temperature for 1 hour. Sugar alcohol concentration in the alcohol solution before and after diatomaceous earth or activated carbon treatment was measured under the same conditions as in Examples 1 to 27 with high performance liquid chromatography (manufactured by Shimadzu Corporation), and sugar alcohol adsorption removal rate was calculated by the same method as in Examples 28 to 72. The results are shown in Table 2.

TABLE 2

| | Alcohol | Sugar alcohol | Sugar alcohol/alcohol (wt %) | Moisture concentration (wt %) | Adsorbent | Removal rate (%) |
|---|---|---|---|---|---|---|
| Ex. 28 | n-Butanol | Glycerol | 1.5 | 0 | NaX | 99 |
| Ex. 29 | | | 1.5 | 0 | NH4/ZSM-5 | 12 |
| Ex. 30 | | | 1.5 | 0 | K/ferrierite | 26 |
| Ex. 31 | | | 1.5 | 0 | NaY | 93 |
| Ex. 32 | | | 1.5 | 0 | Silica-alumina | 27 |
| Ex. 33 | | | 1.5 | 0 | Alumina | 36 |
| Ex. 34 | | | 1.5 | 0 | SA10A | 30 |
| Ex. 35 | | | 1.5 | 0 | SA10AOH | 84 |
| Ex. 36 | | | 1.5 | 0 | WA20 | 13 |
| Ex. 37 | | | 1.5 | 0 | SK1B | 23 |
| Ex. 38 | | | 1.5 | 0 | SK1BH | 24 |
| Ex. 39 | | | 0.5 | 15 | NaX | 11 |
| Ex. 40 | | | 0.5 | 15 | NaY | 15 |
| Ex. 41 | | | 0.5 | 15 | SA10AOH | 55 |
| Ex. 42 | | Xylitol | 0.5 | 15 | NaX | 45 |
| Ex. 43 | | | 0.5 | 15 | NaY | 37 |
| Ex. 44 | | | 0.5 | 15 | SA10AOH | 90 |
| Ex. 45 | 1,4-Butanediol | Glycerol | 1.5 | 0 | NaX | 41 |
| Ex. 46 | | | 1.5 | 0 | NaY | 32 |
| Ex. 47 | | | 1.5 | 0 | Silica-alumina | 12 |
| Ex. 48 | | | 1.5 | 0 | Alumina | 15 |
| Ex. 49 | | | 1.5 | 0 | SA10AOH | 16 |
| Ex. 50 | | | 0.5 | 15 | SA10AOH | 22 |
| Ex. 51 | | Xylitol | 0.5 | 15 | SA10AOH | 49 |
| Ex. 52 | Isopropanol | Glycerol | 1.5 | 0 | NaX | 99 |
| Ex. 53 | | | 1.5 | 0 | NaY | 89 |
| Ex. 54 | | | 1.5 | 0 | Silica-alumina | 26 |
| Ex. 55 | | | 1.5 | 0 | Alumina | 36 |
| Ex. 56 | | | 1.5 | 0 | SA10AOH | 82 |
| Ex. 57 | | | 0.5 | 15 | SA10AOH | 57 |
| Ex. 58 | | Xylitol | 0.5 | 15 | SA10AOH | 95 |
| Ex. 59 | Ethanol | Glycerol | 1.5 | 0 | NaX | 98 |
| Ex. 60 | | | 1.5 | 0 | NaY | 74 |
| Ex. 61 | | | 1.5 | 0 | Silica-alumina | 18 |
| Ex. 62 | | | 1.5 | 0 | Alumina | 26 |
| Ex. 63 | | | 1.5 | 0 | SA10AOH | 53 |
| Ex. 64 | | | 0.5 | 15 | SA10AOH | 47 |
| Ex. 65 | | Xylitol | 0.5 | 15 | SA10AOH | 92 |
| Ex. 66 | 1,3-Propanediol | Glycerol | 1.5 | 0 | NaX | 34 |
| Ex. 67 | | | 1.5 | 0 | NaY | 20 |
| Ex. 68 | | | 1.5 | 0 | Silica-alumina | 11 |
| Ex. 69 | | | 1.5 | 0 | Alumina | 11 |
| Ex. 70 | | | 1.5 | 0 | SA10AOH | 15 |
| Ex. 71 | | | 0.5 | 15 | SA10AOH | 16 |
| Ex. 72 | | Xylitol | 0.5 | 15 | SA10AOH | 31 |
| Comp. Ex. 7 | n-Butanol | Glycerol | 0.5 | 15 | Diatomaceous earth | 3 |
| Comp. Ex. 8 | | | 1.5 | 0 | Activated carbon | 0 |
| Comp. Ex. 9 | | Xylitol | 0.5 | 15 | Diatomaceous earth | 4 |
| Comp. Ex. 10 | 1,4-Butanediol | Glycerol | 0.5 | 15 | Diatomaceous earth | 1 |
| Comp. Ex. 11 | | | 1.5 | 0 | Activated carbon | 0 |
| Comp. Ex. 12 | | Xylitol | 0.5 | 15 | Diatomaceous earth | 1 |

As shown in Table 2, we found that an alcohol solution with sugar alcohol reduced can be obtained by treating an alcohol solution containing sugar alcohol with zeolite, an ion-exchange resin, silica-alumina or alumina.

Example 73

Adsorbent Treatment of Model Alcohol Fermented Solution, and Distillation Test

Pure water was added to 1,500 g of n-butanol, 60 g of phosphoric acid, 7.5 g of glucose, 7.5 g of xylose, 7.5 g of fructose, 7.5 g of glycerol, 7.5 g of xylitol, 10 g of succinic acid, 10 g of lactic acid, 5 g of formic acid, 90 g of acetic acid, 200 g of ethanol and 100 g of ammonium sulfate (all manufactured by Wako Pure Chemical Industries, Ltd.) to prepare 50 L of model n-butanol fermented solution. Subsequently, the model n-butanol fermented solution was concentrated by using a reverse osmosis membrane module SU-810 (manufactured by Toray Industries Inc.) to obtain 85 weight % n-butanol aqueous solution. To 50 g of the 85 weight % n-butanol aqueous solution was added 5 g of NaX type zeolite (F-9, manufactured by Tosoh Corporation), followed by stirring at room temperature for 1 hour. The adsorbent-treated solution was filtered by using qualitative filter paper No. 2 (manufactured by Advantech Co., Ltd.) to separate the adsorbent, thereby a filtrate was recovered. The filtrate obtained was distilled at 130° C. under ordinary pressure to obtain purified n-butanol. The degree of coloration of the purified n-butanol obtained was measured by using color meter for petroleum products OME 2000 (manufactured by Nippon Denshoku Industries Co., Ltd.), and evaluated as APHA (Hazen color number) value. The result is shown in Table 3.

Comparative Example 13

Distillation Test of Model Alcohol Fermented Solution

Concentration by a reverse osmosis membrane and distillation were performed in the same manners as in Example 73, except that the model fermented solution was not treated with an adsorbent. The result is shown in Table 3.

TABLE 3

| | Degree of coloration after distillation (APHA) |
|---|---|
| Ex. 73 | 7 |
| Comp. Ex. 13 | 51 |

As shown in Table 3, we found that even the model alcohol fermented solution can be purified into high quality alcohol having low degree of coloration by treating the fermented solution with zeolite to obtain an alcohol solution having reduced sugar and sugar alcohol and distilling it.

Examples 74 to 88

Adsorption Removal Test of Sugar or Sugar Alcohol in 1,6-Hexanediol Solution by Adsorbent To 1,6-hexanediol (manufactured by Wako Pure Chemical Industries, Ltd.) were added pure water and 0.5 weight % of sugar (glucose, fructose or xylose, all manufactured by Wako Pure Chemical Industries, Ltd.) or sugar alcohol (glycerol or xylitol, both manufactured by Wako Pure Chemical Industries, Ltd.) based on the 1,6-hexanediol to prepare 50 g of 85 weight % 1,6-hexanediol solution. Subsequently, to 50 g of the alcohol solution was added as an adsorbent, 5 g of any of NaX type zeolite (F-9, manufactured by Tosoh Corporation), NaY type zeolite (HSZ-300, manufactured by Tosoh Corporation) and "DIAION" SA10AOH (OH-type strongly basic ion-exchange resin, manufactured by Mitsubishi Chemical Corporation), followed by stirring at room temperature for 1 hour. Sugar or sugar alcohol concentration in the 1,6-hexanediol solution before and after the adsorbent treatment was measured with high performance liquid chromatography, and sugar or sugar alcohol adsorption removal rate was calculated by the method of Formula (1) or Formula (2). The results are shown in Table 4.

Comparative Examples 14 to 23

Adsorption Removal Test of Sugar or Sugar Alcohol in 1,6-Hexanediol Solution by Diatomaceous Earth and Activated Carbon To 1,6-hexanediol (manufactured by Wako Pure Chemical Industries, Ltd.) were added pure water and 0.5 weight % of sugar (glucose, fructose or xylose, all manufactured by Wako Pure Chemical Industries, Ltd.) or sugar alcohol (glycerol or xylitol, both manufactured by Wako Pure Chemical Industries, Ltd.) based on the 1,6-hexanediol to prepare 50 g of 85 weight % 1,6-hexanediol solution. Subsequently, to 50 g of the alcohol solution was added 5 g of diatomaceous earth ("Celite 545", manufactured by Kanto Chemical Co., Inc.) or 0.1 g of activated carbon ("SHIRASAGI A", manufactured by Japan Enviro Chemicals, Ltd.), followed by stirring at room temperature for 1 hour. Sugar or sugar alcohol concentration in the 1,6-hexanediol solution before and after the diatomaceous earth or activated carbon treatment was measured with high performance liquid chromatography, and sugar or sugar alcohol adsorption removal rate was calculated by the method of Formula (1) or Formula (2). The results are shown in Table 4.

TABLE 4

| | Alcohol | Sugar or sugar alcohol | Sugar or sugar alcohol/alcohol (wt %) | Moisture concentration (wt %) | Adsorbent | Removal rate (%) |
|---|---|---|---|---|---|---|
| Ex. 74 | 1,6-Hexanediol | Glucose | 0.5 | 15 | NaX | 82 |
| Ex. 75 | | | 0.5 | 15 | NaY | 57 |
| Ex. 76 | | | 0.5 | 15 | SA10AOH | 94 |
| Ex. 77 | | Fructose | 0.5 | 15 | NaX | 81 |
| Ex. 78 | | | 0.5 | 15 | NaY | 66 |
| Ex. 79 | | | 0.5 | 15 | SA10AOH | 97 |
| Ex. 80 | | Xylose | 0.5 | 15 | NaX | 56 |

TABLE 4-continued

| | Alcohol | Sugar or sugar alcohol | Sugar or sugar alcohol/alcohol (wt %) | Moisture concentration (wt %) | Adsorbent | Removal rate (%) |
|---|---|---|---|---|---|---|
| Ex. 81 | | | 0.5 | 15 | NaY | 30 |
| Ex. 82 | | | 0.5 | 15 | SA10AOH | 97 |
| Ex. 83 | | Glycerol | 0.5 | 15 | NaX | 16 |
| Ex. 84 | | | 0.5 | 15 | NaY | 18 |
| Ex. 85 | | | 0.5 | 15 | SA10AOH | 39 |
| Ex. 86 | | Xylitol | 0.5 | 15 | NaX | 64 |
| Ex. 87 | | | 0.5 | 15 | NaY | 51 |
| Ex. 88 | | | 0.5 | 15 | SA10AOH | 80 |
| Comp. Ex. 14 | | Glucose | 0.5 | 15 | Diatomaceous earth | 0 |
| Comp. Ex. 15 | | | 0.5 | 15 | Activated carbon | 1 |
| Comp. Ex. 16 | | Fructose | 0.5 | 15 | Diatomaceous earth | 0 |
| Comp. Ex. 17 | | | 0.5 | 15 | Activated carbon | 0 |
| Comp. Ex. 18 | | Xylose | 0.5 | 15 | Diatomaceous earth | 1 |
| Comp. Ex. 19 | | | 0.5 | 15 | Activated carbon | 0 |
| Comp. Ex. 20 | | Glycerol | 0.5 | 15 | Diatomaceous earth | 1 |
| Comp. Ex. 21 | | | 0.5 | 15 | Activated carbon | 1 |
| Comp. Ex. 22 | | Xylitol | 0.5 | 15 | Diatomaceous earth | 1 |
| Comp. Ex. 23 | | | 0.5 | 15 | Activated carbon | 2 |

As shown in Table 4, we found that 1,6-hexanediol solution having reduced sugar or sugar alcohol can be obtained by treating 1,6-hexanediol solution containing sugar or sugar alcohol with zeolite or an ion-exchange resin.

INDUSTRIAL APPLICABILITY

Sugar impurities contained as impurities in an alcohol solution can be reduced with high efficiency at low cost, and high quality alcohol in which coloration by heating during distillation has been reduced can be obtained.

The invention claimed is:

1. A method of producing a purified alcohol comprising contacting an alcohol solution comprising sugar and/or sugar alcohol as impurities and comprising an alcohol other than sugar alcohol in a concentration of 50 weight % or more, with one or a mixture of two or more adsorbents selected from the group consisting of zeolite, an ion-exchange resin, silica-alumina and alumina, thereby adsorbing the sugar and/or sugar alcohol, and recovering an alcohol solution that has not been adsorbed.

2. The method according to claim 1, wherein the alcohol other than sugar alcohol is a monohydric or dihydric alcohol.

3. The method according to claim 1, wherein the alcohol other than sugar alcohol is an alcohol having 2 to 6 carbon atoms.

4. The method according to claim 1, wherein the alcohol other than sugar alcohol is one or a mixture of two or more alcohols selected from the group consisting of ethanol, ethylene glycol, isopropanol, 1,3-propanediol, n-butanol, 2-butanol, isobutanol, 1,4-butanediol, 2,3-butanediol and 1,6-hexanediol.

5. The method according to claim 1, wherein the alcohol solution contains glucose, fructose or xylose as impurities.

6. The method according to claim 1, wherein the alcohol solution contains glycerol, xylitol or erythritol as impurities.

7. The method according to claim 1, wherein an inlet pore diameter of the zeolite is larger than 5 angstroms.

8. The method according to claim 1, wherein the ion-exchange resin is a strongly basic ion-exchange resin.

9. The method according to claim 1, further comprising distilling the alcohol solution from which the sugar and/or sugar alcohol have been adsorbed and removed.

10. The method alcohol according to claim 2, wherein the alcohol other than sugar alcohol is an alcohol having 2 to 6 carbon atoms.

11. The method according to claim 2, wherein the alcohol other than sugar alcohol is one or a mixture of two or more alcohols selected from the group consisting of ethanol, ethylene glycol, isopropanol, 1,3-propanediol, n-butanol, 2-butanol, isobutanol, 1,4-butanediol, 2,3-butanediol and 1,6-hexanediol.

12. The method according to claim 2, wherein the alcohol solution contains glucose.

13. The method according to claim 2, wherein the alcohol solution contains glycerol, xylitol or erythritol as impurities.

14. The method according to claim 2, wherein an inlet pore diameter of the zeolite is larger than 5 angstroms.

15. The method according to claim 2, wherein the ion exchange resin is a strongly basic ion-exchange resin.

16. The method according to claim 2, further comprising distilling the alcohol solution from which the sugar and/or sugar alcohol have been adsorbed and removed.

* * * * *